US008550989B2

(12) United States Patent
Dohi et al.

(10) Patent No.: US 8,550,989 B2
(45) Date of Patent: Oct. 8, 2013

(54) FLEXIBILITY/RIGIDITY ADJUSTABLE APPARATUS

(75) Inventors: Takeyoshi Dohi, Tokyo (JP); Ken Masamune, Tokyo (JP); Siyang Zuo, Tokyo (JP); Kiyoshi Matsumiya, Tokyo (JP); Noriaki Yamanaka, Tokyo (JP)

(73) Assignee: The University of Tokyo, Tokyo (JP)

( * ) Notice: Subject to any disclaimer, the term of this patent is extended or adjusted under 35 U.S.C. 154(b) by 328 days.

(21) Appl. No.: 12/866,769

(22) PCT Filed: Feb. 27, 2009

(86) PCT No.: PCT/JP2009/053719
§ 371 (c)(1),
(2), (4) Date: Aug. 9, 2010

(87) PCT Pub. No.: WO2009/107792
PCT Pub. Date: Sep. 3, 2009

(65) Prior Publication Data
US 2010/0324370 A1 Dec. 23, 2010

(30) Foreign Application Priority Data
Feb. 29, 2008 (JP) .................... 2008-049701

(51) Int. Cl.
*A61B 1/00* (2006.01)
(52) U.S. Cl.
USPC .......... 600/144; 600/114; 600/121; 600/125; 600/148
(58) Field of Classification Search
USPC .............. 600/114, 121–125, 138–139, 144, 600/148
See application file for complete search history.

(56) References Cited

U.S. PATENT DOCUMENTS

| 5,337,733 A * | 8/1994 | Bauerfeind et al. | 600/139 |
| 6,790,173 B2 * | 9/2004 | Saadat et al. | 600/144 |
| 6,837,846 B2 * | 1/2005 | Jaffe et al. | 600/114 |
| 2007/0208224 A1 * | 9/2007 | Olson | 600/139 |

FOREIGN PATENT DOCUMENTS

| JP | 63-46688 | 9/1988 |
| JP | 11-276425 | 10/1999 |

(Continued)

*Primary Examiner* — Matthew J Kasztejna
*Assistant Examiner* — Kevin G Barry, III
(74) *Attorney, Agent, or Firm* — Boyle Fredrickson, S.C.

(57) ABSTRACT

There is provided a flexibility/rigidity adjustable apparatus which can change over its state between a flexible state in which such apparatus is freely bendable and a rigid state in which such bending is restricted when in use. A flexible closing cover 18 which can expand/shrink is provided on an outer circumference 2 of a flexible tube 1. A latching member 7 which moves together with the closing cover 18 is provided, and a latching-member receiving part 11 with which the latching member 7 can engage is provided at the outer circumference 2 of the tube 1. A closed space 21 formed between the closing cover 18 and the tube 1 is connected to an air inlet/outlet part 22. As the air is evacuated through the inlet/outlet part 22 to change the pressurized condition of the closed space 21 from an atmospheric pressure condition to a negative pressure condition, the closing cover 18 reduces its diameter around an axis 4, and the latching member 7 is caused to engage with the latching-member receiving part 11. As air is supplied in the closed space 21 to make the interior thereof in an atmospheric pressure condition, the closing cover 18 expands, and engagement of latching member 7 with the latching-member receiving part 11 is released, so that the tube 1 becomes a flexible state from a rigid state.

11 Claims, 12 Drawing Sheets

(56) References Cited

FOREIGN PATENT DOCUMENTS

| JP | 3132800 | 2/2001 |
| JP | 2005-046273 | 2/2005 |
| JP | 2005-318957 | 11/2005 |

* cited by examiner

FLEXIBILITY/RIGIDITY ADJUSTABLE APPARATUS

TECHNICAL FIELD

The present invention relates to a flexibility/rigidity adjustable apparatus which can change its state between a flexible state and a rigid state, and which is used in the fields of medical engineering, in particular, laparoscopic surgeries, such as a surgical treatment of various deep locations inside a body, a flexible endoscopic treatment, and an MRI treatment.

BACKGROUND ART

Laparoscopic surgery of opening several tiny stomata in an abdominal area and of inserting a surgical instrument having an endoscope and a shaft is less invasive in comparison with conventional abdominal surgical operations. However, such surgical instruments have a restricted motion with a low degree of freedom supported around an insertion stoma. Moreover, because most instruments are in a long linear shape, when a diseased part is present deep inside a body, it is difficult to directly approach such diseased part. In general, in abdominal endoscopic surgery, a peritoneal membrane is lifted to secure a large operative field space inside a body, and a surgical instrument is linearly inserted to have a medical treatment. However, securing of a large operative field space inside the body is a problem itself, which brings about a complicating disease due to carbon dioxide in the case of pneumoperitoneum surgery. Moreover, because most instruments are in a long liner shape, when a diseased part is present deep inside a body, it is difficult to directly approach such diseased part. Furthermore, even if a large operative field is secured, straight approach to such diseased part is difficult in some cases.

In order to overcome such a problem, a so-called flexible tube which can freely bend may be used. However, when external force is applied, the flexible tube is deformed, which leaves a problem that it becomes difficult to maintain a condition in which a peritoneal membrane is being lifted to secure a large operative field space inside a body. In order to overcome this problem, there is proposed a flexible tube having concavities and convexities formed on the outer circumferential surface along the axial direction, and a bending restriction piece having a protrusion fitted into the concavity is linearly attached to the flexible tube (see, for example, patent literature 1).
Patent Literature 1: Japan Patent No. 3132800

DISCLOSURE OF INVENTION

Problem to be Solved by the Invention

The flexible tube of the conventional technology is, when in use, bent in a predetermined shape with the bending restriction piece being attached to the flexible tube beforehand. Accordingly, for example, once the flexible tube in a flexible state is inserted, it is difficult to change the state of such a tube to a rigid state in order to maintain such an insertion condition. Hence, the degree of freedom for use of the flexible tube is low.

It is an object of the present invention to provide a flexibility/rigidity adjustable apparatus which can change its state between a flexible state in which such apparatus is freely bendable and a rigid state in which bending of such apparatus is restricted. Moreover, it is another object of the present invention to ensure restriction of bending in the rigid state of the flexibility/rigidity adjustable apparatus and to enable changing of the state between the flexible state and the rigid state through a simple operation. Furthermore, it is the other object to provide an apparatus which can cause a flexible surgical instrument to go around an important tissue inside a body and to safely reach a diseased part, and which enables safe replacement of such surgical instrument.

Means for Solving the Problem

In order to accomplish the foregoing objects, a flexibility/rigidity adjustable apparatus according to a first aspect comprises: a flexible, long and thin member; a closing cover which covers an exterior of an outer circumference of the long and thin member, and which is able to expand/shrink around an axis of the long and thin member; a fluid inlet/outlet part connected to a closed space formed between the closing cover and the outer circumference of the long and thin member; and a latching member which is able to, together with a shrinkage operation of the closing cover, engage with a latching-member receiving part provide at the outer circumference of the long and thin member.

According to the flexibility/rigidity adjustable apparatus of the second aspect of the present invention, the long and thin member is a tube having a leading end and a basal end opposite to the leading end both opened.

According to the flexibility/rigidity adjustable apparatus of the third aspect of the present invention, the latching member is provided outwardly of the tube so as to protrude toward the axis of the tube.

According to the flexibility/rigidity adjustable apparatus of the fourth aspect of the present invention, the latching-member receiving part is provided so as to face the latching member and so as to protrude in a direction opposite to the axis of the tube.

According to the flexibility/rigidity adjustable apparatus of the fifth aspect of the present invention, the basal end of the tube is provided with the fluid inlet/outlet part.

According to the flexibility/rigidity adjustable apparatus of the sixth aspect of the present invention, the latching member is formed together with the closing cover.

According to the flexibility/rigidity adjustable apparatus of the seventh aspect of the present invention, further comprises a holding member which is provided around the outer circumference of the tube and which makes the latching member flexible, wherein the holding member is installed between spacers fixed along a lengthwise direction of the axis of the tube with a clearance.

According to the flexibility/rigidity adjustable apparatus of the eighth aspect of the present invention, further comprises a direction regulating member, which has one end coupled to a leading end of the tube, is provided along a lengthwise direction of the axis of the tube, and has another end provided at the basal end side of the tube.

According to the flexibility/rigidity adjustable apparatus of the ninth aspect of the present invention, the latching member and the latching-member receiving part facing the latching member are provided in at least two radiation directions around the axis of the tube.

According to the flexibility/rigidity adjustable apparatus of the tenth aspect of the present invention, further comprises an opening/closing body which opens/closes the opening of the leading end of the tube.

According to the flexibility/rigidity adjustable apparatus of the eleventh aspect of the present invention, wherein all of the structural elements are formed of a non-magnetic material.

According to the flexibility/rigidity adjustable apparatus of the twelfth aspect of the present invention, wherein a basal end of the direction regulating member is coupled to a motor-driven driving device.

According to the flexibility/rigidity adjustable apparatus of the thirteenth aspect of the present invention, wherein a clearance between adjoining spacers is set to be narrower at the leading end side of the long and thin member than at other portions of the long and thin member.

According to the flexibility/rigidity adjustable apparatus of the fourteenth aspect of the present invention, wherein a fiber scope is inserted in the long and thin member.

Effect of the Invention

According to the flexibility/rigidity adjustable apparatus of the first aspect of the present invention, as the pressurized condition of the closed space is changed from an atmospheric pressure condition to a negative pressure condition, the closing cover reduces its diameter around the axis, and the latching member is caused to engage with the latching-member receiving part, thereby changing the state from a flexible state to a rigid state. Conversely, as the pressurized condition of the closed space is changed from a negative pressure condition to an atmospheric pressure condition, the closing cover increases its diameter around the axis, engagement of the latching member with the latching-member receiving part is released, thereby changing the state from a rigid state to a flexible state. In this fashion, a change in fluid pressure in the closed space is utilized to change the state between a flexible state and a rigid state.

According to the flexibility/rigidity adjustable apparatus of the second aspect of the present invention, a flexible surgical instrument inserted from the opening at the basal end side can be allowed to protrude from the opening at the leading end side through the tube.

According to the flexibility/rigidity adjustable apparatus of the third and fourth aspects of the present invention, as the latching member and the latching-member receiving part are protrusions, engagement therebetween is ensured in comparison with a case in which both pieces are flat.

According to the flexibility/rigidity adjustable apparatus according to the fifth aspect of the present invention, an air intake/exhaust operation can be controlled at the basal end side of the tube, so that an operation of adjusting pressure in the closed space is facilitated.

According to the flexibility/rigidity adjustable apparatus according to the sixth aspect of the present invention, as the latching member is formed together with the closing cover, any mechanism of transmitting power therebetween becomes unnecessary, so that it is possible to reduce the number of parts and to reduce the size of the flexibility/rigidity adjustable apparatus, thereby improving the failure rate.

According to the flexibility/rigidity adjustable apparatus according to the seventh aspect of the present invention, as the holding member attached through a spacer is provided with the latching member, positioning of the holding member, and thus positioning of the latching member become precise, so that engagement between the latching member and the latching-member receiving part and releasing thereof can be ensured.

According to the flexibility/rigidity adjustable apparatus according to the eighth aspect of the present invention, it is possible to change the direction of the leading end of the tube in a flexible state by manipulating the direction regulating member at the basal end side.

According to the flexibility/rigidity adjustable apparatus according to the ninth aspect of the present invention, as the latching member and the latching-member receiving part are provided in at least two radiation direction around the axis, those pieces are engaged with each other in at least two radiation direction around the axis of the tube to secure a rigid state.

According to the flexibility/rigidity adjustable apparatus according to the tenth aspect of the present invention, when the tube is inserted in, for example, a body, as the opening in the leading end is covered by the opening/closing body, the hollow condition in the tube can be secured.

According to the flexibility/rigidity adjustable apparatus according to the eleventh aspect of the present invention, any negative effect inherent to the structure of such apparatus even under an environment utilizing nuclear magnetic resonance can be suppressed.

According to the flexibility/rigidity adjustable apparatus according to the twelfth aspect of the present invention, the direction regulating member can be remotely manipulated.

According to the flexibility/rigidity adjustable apparatus according to the thirteenth aspect of the present invention, the leading end of the long and thin member in a rigid state can have enhanced strength.

According to the flexibility/rigidity adjustable apparatus according to the fourteenth aspect of the present invention, visual checking is enabled by a fiber scope.

BEST MODE FOR CARRYING OUT THE INVENTION

An explanation will be given of preferred embodiments of the present invention with reference to the accompanying drawings.

First Embodiment

FIGS. 1 to 7 show a first embodiment. A flexibility/rigidity adjustable apparatus of the present embodiment is a outer sheath which is a device for securing an entering path of a flexible surgical instrument, and the outer sheath is inserted in a body in a flexible state and is caused to become hard in an arbitrary shape after reaching a target diseased part, thereby securing a path through which a flexible surgical instrument A can pass.

Figure 1:
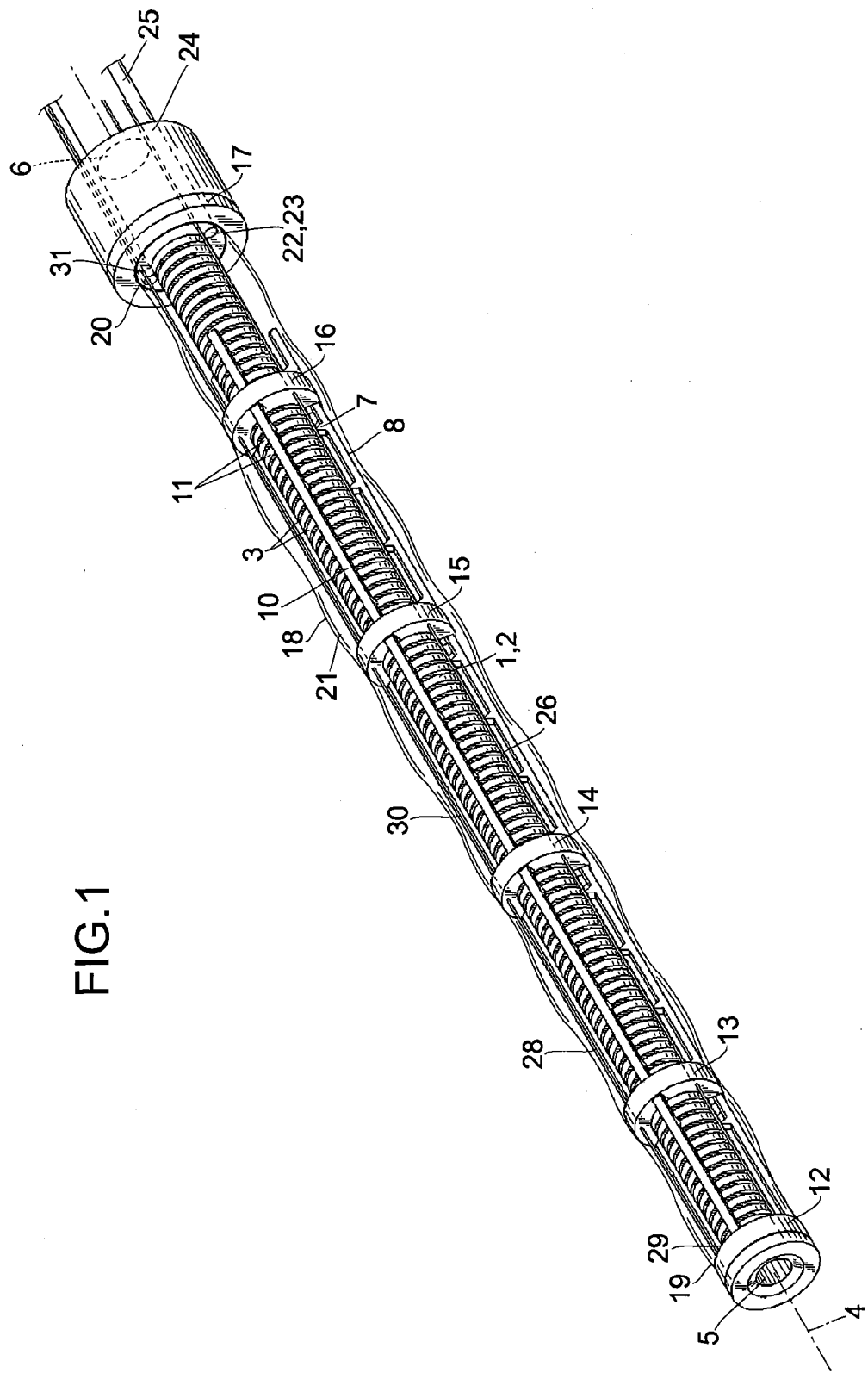
FIG. 1 is a perspective view showing a first embodiment of the present invention in a straight condition with a closing cover being partially cut out.
Figure 2:
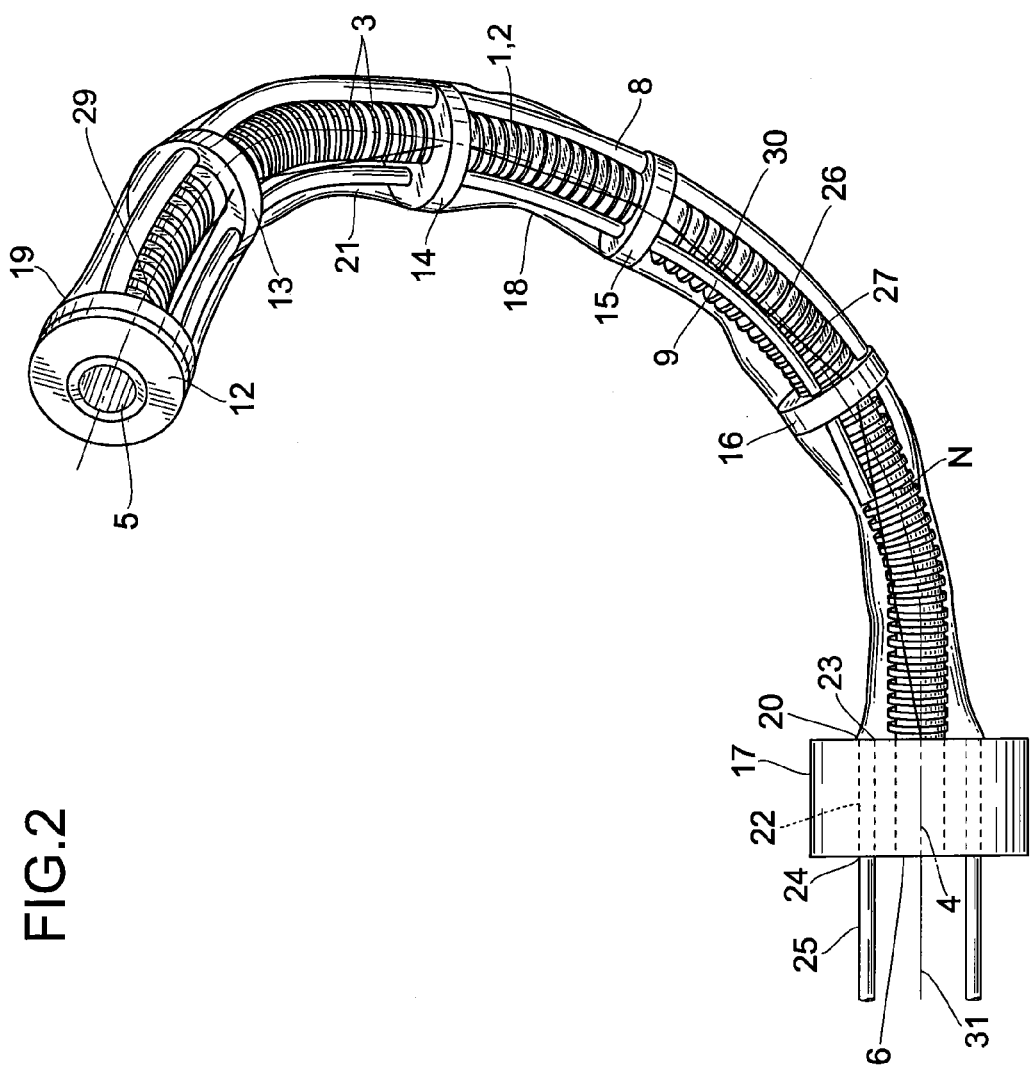
FIG. 2 is a perspective view in a bent condition with the closing cover being partially cut out.

FIG. 1 is a perspective view showing a straight condition before bent, and FIG. 2 shows a bent condition. A tube 1 which is a long and thin member formed of a synthetic resin has protrusions 3 successively formed on an outer circumference 2 along the lengthwise direction of a center axis 4, and the protrusions 3 are each formed in an annular shape around the axis 4 directed to the external side. Accordingly, a bellows tube having protrusions 3 with a square cross section formed successive in a concavo-convex wavy shape on the outer circumference 2 is formed, so that the tube 1 is formed as bendable bellows with flexibility. A leading-end opening 5 is formed in a leading end face of the tube 1, while a basal-end opening 6 is formed in a basal end of the tube 1 opposite to the leading end.

Furthermore, latching members 7 are provided outwardly of the outer circumference 2 of the tube 1. As shown in FIGS. 3 to 6, the latching members 7 are each a protrusion in a sawtooth-like shape having a leading end becoming narrow toward the axis 4 side, and the plural latching members 7 are provided along the lengthwise direction of the axis 4. First to third holding members 8, 9, and 10 are each provided with the latching members 7 aligned along the lengthwise direction of the axis 4 with clearances. The first to third holding members 8, 9, and 10 are provided in plural direction, in the case of the present embodiment, in three directions at a clearance of 120 degree around the axis 4. The holding members 8, 9, and 10 are each formed together with the latching members 7 from a synthetic resin, and each has flexibility and restoring elastic force to return to the linear shape.

The latching member 7 can selectively engage with any one of the protrusions 3, and it is illustrated in the figure that the protrusion 3 located a position where the latching member 7 engages is a latching-member receiving part 11. A length L of the latching member 7 in the lengthwise direction of the axis 4 is shorter than a clearance M between the adjoining protrusions 3 (latching-member receiving parts 11) (L<M), so that the latching member 7 can fit in the clearance between the protrusions 3 (latching-member receiving parts 11) and is engaged therewith.

Spacers 12, 13, 14, 15, 16, and 17 in a ring-shape around the axis 4 are provided at the outer circumference 2 of the tube 1, and a closing cover 18 is provided outwardly of those spacers 12, etc. The first to sixth spacers 12, 13, 14, 15, 16, and 17 are provided from the leading end of the tube 1 toward the basal end thereof. The first spacer 12 is fixed to the outer circumference 2 of the leading end of the tube 1, the second to fifth spacers 13, 14, 15, and 16 are fixed to the middle part of the tube 1 with clearances, and the sixth spacer 17 is provided at the basal end of the tube 1. The holding members 8, 9, and 10 are installed between the first spacer 12 to the fifth spacer 16 in such a manner as to pass all the way through the second to fourth spacers 13, 14, 15, and 16. The first to fifth spacers 12, 13, 14, 15, and 16 are provided between the tube 1 and the holding members 8, 9, and 10 so as to prevent the latching member 7 from contacting adjacent latching-member receiving part 11 when the tube 1 is in a flexible state.

Furthermore, the closing cover 18 is provided outwardly of the outer circumference 2 of the tube 1. The closing cover 18 is formed of, for example, a bag-like synthetic resin, is formed in a flexible, long and thin tubular shape, and covers the outer circumference 2 and the holding members 8, 9, 10 across the whole length of the tube 1 along the lengthwise direction of the axis 4 with some margin wrinkles. A leading end 19 of the closing cover is airtightly connected to the outer circumference 2 of the leading end of the tube 1. The closing cover 18 is formed of a synthetic resin like a polyethylene sheet (or a film) in the present embodiment and has flexibility, but may be formed of an elastic sheet (or a film) like a rubber balloon having flexibility and elasticity.

The leading end 19 side of the closing cover 18 is airtightly coupled to the first spacer 12. The middle part of the closing cover 18 covers the exteriors of respective second to fifth spacers 13, 14, 15, and 16, so that the second to fifth spacers 13, 14, 15, and 16 are present between the tube 1 and the holding members 8, 9, and 10 in order to prevent the latching member 7 from contacting the adjacent latching-member receiving part 11 when the tube 1 is in a flexible state. Conversely, the basal end 20 side of the closing cover 18 is airtightly coupled to the sixth spacer 17. Accordingly, the sixth spacer 17 is present between the tube 1 and the closing cover 18 so as to prevent the tube 1 from contacting the closing cover 18 when the tube 1 is in a flexible state.

Furthermore, the sixth spacer 17 is provided with inlet/outlet parts 22 for taking in/out a fluid, e.g., in the present embodiment, air, relative to a closed space 21 surrounded by the outer circumference 2 of the tube 1 and the closing cover 18. In the present embodiment, the inlet/outlet parts are provided as a symmetrical pair so as to pass all the way through the sixth spacer 17 in the lengthwise direction of the axis 4, and an internal end 23 of the inlet/outlet part 22 is provided so as to communicate with the closed space 21, while an external end 23 of the inlet/outlet part is connected to intake/exhaust means (not illustrated) via an intake/exhaust tube 25. The inlet/outlet part 22 is used for both intake and exhaust in the present embodiment, but separate parts for intake or exhaust may be provided.

First to third direction regulating members 26, 27, and 28 which direct the leading end of the tube 1 to a desired direction are provided along the tube 1. The first to third direction regulating members 26, 27, and 28 are each a line member or a bar member, such as a fishing line formed of a synthetic resin or a wire, e.g., a fluorocarbon wire, have flexibility in either case. Each direction regulating member has a leading end 29 coupled to the leading end of the tube 1, has a middle part 30 passing all the way through the second to fifth spacers 13, 14, 15, and 16 in a slidable manner along the lengthwise direction of the axis 4, and has another end 31 protruding outwardly from the sixth spacer 17 while passing all the way therethrough in a slidable manner. The first to third direction regulating members 26, 27, and 28 are provided in three directions shifted from respective positions of the first to third holding members 8, 9, and 10 with a clearance of 120 degree around the axis 4.

Figure 3:
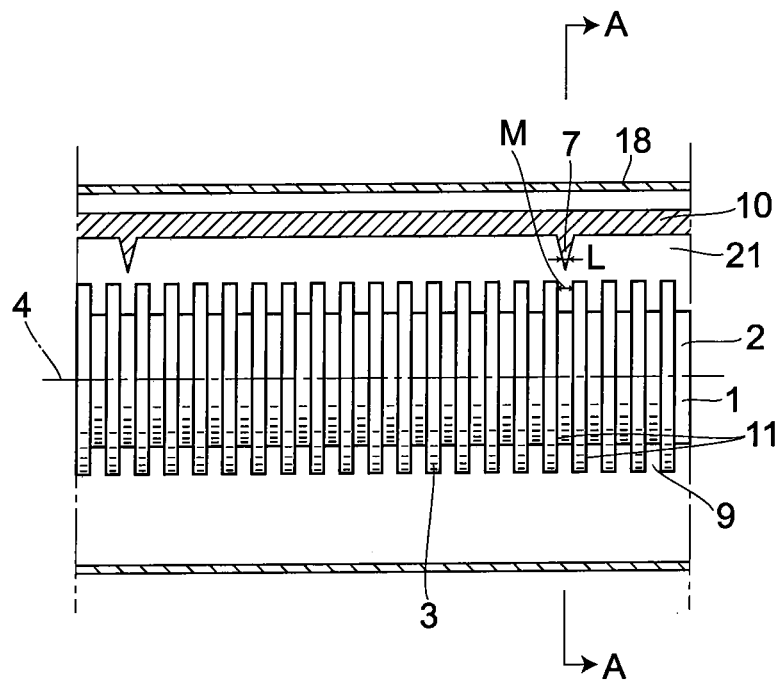
FIG. 3 is a cross-sectional view showing a flexible state.
Figure 4:
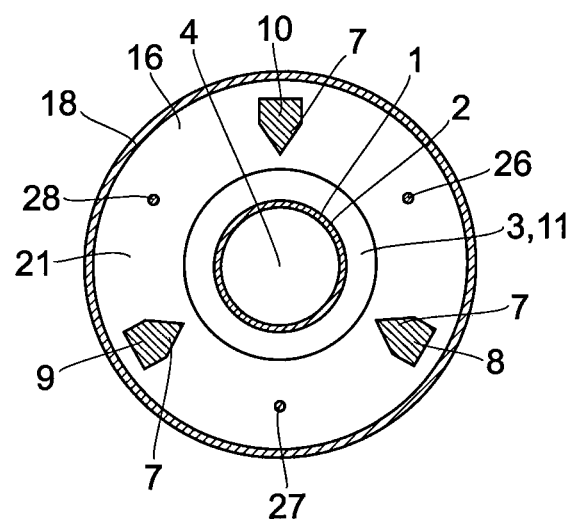
FIG. 4 is a cross-sectional view along a line A-A in FIG. 3.
Figure 7:
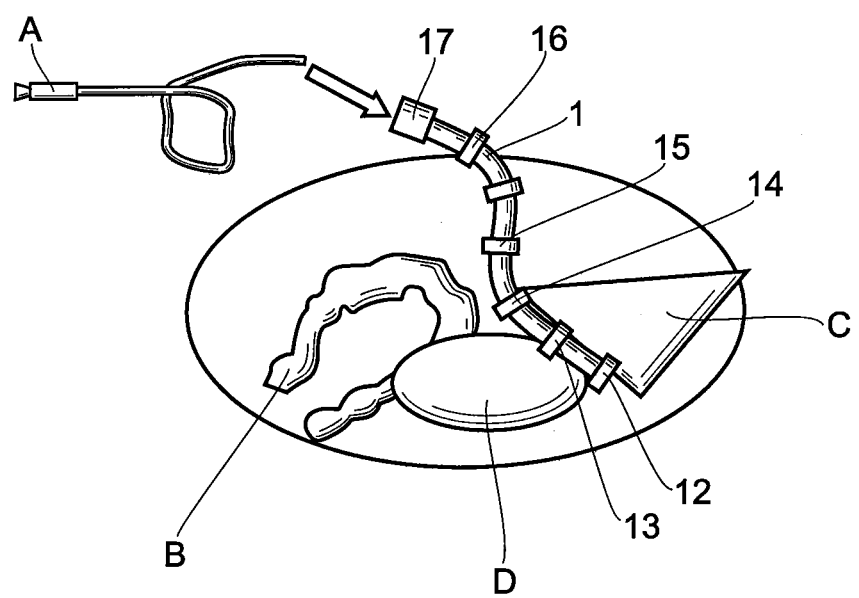
FIG. 7 is an explanatory diagram for a use situation.

Next, an explanation will be given of the working and effect of the above-explained structure. In order to secure an entering path for the flexible surgical instrument A, the whole tube 1 having undergone sterilization beforehand is inserted in a body from the leading end side. At this time, as shown in FIGS. 3 and 4, the internal pressure of the closed space 21 is kept at atmospheric pressure, so that the closing cover 18 does not shrink (reduce its diameter) toward the axis 4. As a result, the holding members 8, 9, and 10 installed across the first to fifth spacers 12, 13, 14, 15, and 16 do not pressed inwardly, and the latching member 7 is maintained so as to be spaced apart from the lathing-member receiving part 11. Note that the interior of the closed space may be kept at pressure higher than the atmospheric pressure. Therefore, the tube 1 maintains the flexibility and is in a flexible state. In this flexible state, when, for example, another end 31 of the first direction regulating member 26 is pulled outwardly, the leading end of the tube 1 changes its direction so as to roll back toward the lengthwise direction side of the first direction regulating member 26. Likewise, as the second and third direction regulating members 27, 28 are manipulated, as shown in FIG. 2, the direction of the leading-end opening 5 of the tube 1 can be set freely. Accordingly, as shown in FIG. 7, for example, the leading end of the outer sheath (tube 1) can be arranged between a liver C and a stomach D so that the outer sheath goes around the liver C while avoiding being located at a bowel B side.

Figure 5:
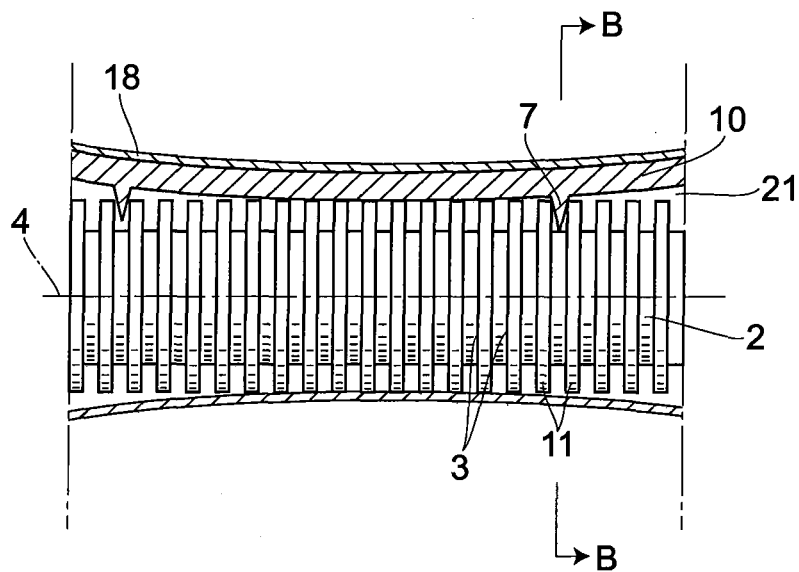
FIG. 5 is a cross-sectional view showing a rigid state.
Figure 6:
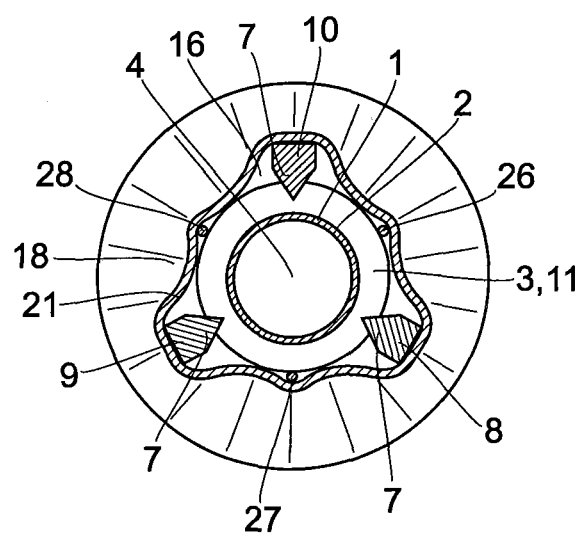
FIG. 6 is a cross-sectional view along a line B-B in FIG. 5.

After the tube 1 in such a flexible state is arranged at a desired location, the tube 1 is hardened and fixed into a rigid state before the flexible surgical instrument A is inserted in the tube 1. Regarding such changing from the flexible state to the rigid state, air inside the closed space 21 is evacuated to the exterior via the inlet/outlet parts 22 to make the interior of the closed space 21 in a negative pressure (vacuumed) condition. Accordingly, the closing cover 18 is depressed by external atmospheric pressure and reduces its diameter. Because of such diameter reduction of the closing cover 18, the holding members 8, 9, and 10 installed across the first to fifth spacers 12, 13, 14, 15, and 16 are pressed in the direction toward the axis 4. At this time, portions of the holding members 8, 9, and 10 supported by the first to fifth spacers 12, 13, 14, 15, and 16 are not pressed, but portions of the holding members 8, 9, and 10 present between first to fifth spacers 12, 13, 14, 15, and 16 reduce its diameter. As a result, as shown in FIGS. 5 and 6, the latching members 7 are fitted in respective clearances M between protrusions 3, and are engaged with respective latching-member receiving parts 11 arranged back and forth in the lengthwise direction of the axis 4, and the latching members 7 are fixed by the first to fifth spacers 12, 13, 14, 15, and 16 through the holding members 8, 9, and 10, so that the portion of the tube 1 around the lathing-member receiving part 11 can be in a fixed condition. As the latching members 7 are engaged with respective latching-member receiving parts 11 intermittently in the lengthwise direction of the tube 1 and are fixed, the tube 1 becomes a rigid state. As the flexible surgical instrument A is inserted from the basal-end opening 6 side of the tube 1 in the rigid state, the leading end of the flexible surgical instrument A can protrude from the leading-end opening 5 while the flexible surgical instrument A running along the bending of the tube 1, and can approach a diseased part. In the present embodiment, the explanation was given of a case in which the flexibility/rigidity adjustable apparatus is used for an abdominal area, but can be applied to cardiac surgery or other sites.

Regarding removal of the tube 1 after the flexible surgical instrument A is pulled out, air is introduced from the inlet/outlet parts 22 to make the closed space 21 expanded, and this expansion causes the closing cover 18 to expand in a direction opposite to the axis 4 (increases its diameter), thereby cancelling depression of the holding members 8, 9, and 10 and thus the latching members 7 in the direction toward the axis 4. Accordingly, the holding members 8, 9, and 10 return to a straight condition, engagement of the latching members 7 with respective latching-member receiving parts 11 are released as the latching members 7 move toward the external side, and as a result, the outer sheath (tube 1) returned to the flexible condition can be pulled out.

As explained above, according to the present embodiment, the flexible closing cover 18 which can expand and shrink is provided on the outer circumference 2 of the flexible tube 1, and the inlet/outlet parts 22 are connected to the closed space 21 formed between the closing cover 18 and the tube 1, the latching members 7 which move together with the closing cover 18 are provided, and the latching-member receiving parts 11 where respective latching members 7 can engage are provided at the outer circumference 2 of the tube 1. Accordingly, as the pressurized condition of the closed space 21 is changed from an atmospheric pressure condition to a negative pressure condition by causing air to be evacuated through the inlet/outlet parts 22, the closing cover 18 reduces its diameter around the axis 4, the latching members 7 are caused to engage with respective latching-member receiving parts 11, and the state of the tube can be changed from the flexible state to the rigid state by exhaustion of air. Therefore, when the tube 1 is inserted in a body, the tube can be set in a flexible state by taking in/out of air, and after insertion, as air is removed, the tube 1 can be freely set in a rigid state.

Moreover, as the tube 1 has the leading-end opening 5 and the basal-end opening 6 formed in the leading end and the basal end, respectively, if the flexible surgical instrument A is inserted in the tube 1 in a rigid state from the basal end thereof and is caused to protrude from the leading end of the tube, the tube can be used as a flexibility/rigidity adjustable outer sheath for the flexible surgical instrument A, and the flexible surgical instrument A can be caused to reach a diseased part by the tube 1 in a rigid state. As the flexible surgical instrument A is caused to reach a diseased part while going around an organ through such outer sheath, it becomes possible to approach the diseased part without deteriorating a positional relationship among tissues in a body, and once such an apparatus is so arranged as to reach the diseased part, the flexible surgical instrument A can be infinitely often replaced within a surgical space for the diseased part where it is difficult to linearly approach without hurting any organs, thereby realizing a less-invasive treatment.

Furthermore, as the latching member 7 and the latching-member receiving part 11 positioned by the first to third holding members 8, 9, and 10, and the tube 1, respectively, in the lengthwise direction of the axis 4 are a protrusion extending in the direction toward the axis 4 and a protrusion extending toward a direction opposite to the axis 4, respectively, when the latching member 7 and the latching-member receiving part 11 engage together, both pieces do not slide in the lengthwise direction of the axis 4, thereby enabling the tube 1 in a rigid state to withstand against any external influences like external force.

Moreover, in the present embodiment, as the inlet/outlet parts 22 for air are provided at the basal end of the tube 1, taking in/out of air relative to the closed space 21 can be controlled at a basal end side located outside a body, so that changing of a state of the tube 1 between a flexible state and a rigid state can be freely controlled at the exterior of the body. Moreover, as the latching member 7 directly contacts the closing cover 18 via the holding member 8, 9, and 10, working force inherent to diameter reduction/increasing of the closing cover 18 is directly transmitted to the latching member 7, so that any additional mechanism of transmitting such working force is unnecessary. Accordingly, the number of parts can be reduced, and the dimension of the apparatus can be reduced, which leads to, for example, thinning of the apparatus, thereby improving a failure rate along with such reduction.

Regarding attachment of the latching member 7, the holding members 8, 9, and 10 causing the latching member 7 to be flexible are provided in the lengthwise direction of the axis 4 outwardly of the outer circumference 2 of the tube 1, and the holding members 8, 9, and 10 are installed across the first to fifth spacers 12, 13, 14, 15, and 16 fixed to the tube 1. For example, between the first and second spacers 12, 13, a linkage-like member is formed by the first and second spacers 12, 13 and the holding members 8, 9, and 10 therebetween, and linkage-like members are successively formed by other spacers 14, 15, 16, and 17 in the same fashion, and the holding members 8, 9, and 10 provided with latching members 7 are each in a condition in which both ends are held by the first to fifth spacers 12, 13, 14, 15, and 16. Accordingly, when the closed space 21 returns to an atmospheric pressure condition from a reduced pressure condition, the holding members 8, 9, and 10 directly return to a straight condition inherent to diameter increasing of the closing cover 18, and engagement of the latching member 7 with the latching-member receiving part 11 can be surely released, thereby ensuring the tube to return to a flexible state from a rigid state.

Furthermore, as the direction regulating members 26, 27, and 28 each having one end 29 coupled to the leading end of the tube 1 are provided along the lengthwise direction of the axis 4 and another end 31 of each direction regulating member 26, 27, and 18 is provided at the basal end side of the tube 1, the direction of the leading end of the tube can be changed by manipulating individual direction regulating members 26, 27, and 28 at the basal end side, so that the direction of the tube 1 in both flexible and rigid states can be freely set.

Still further, as the tube 1, the closing cover 18, the latching members 7, the latching-member receiving parts 11, the holding members 8, 9, and 10, the direction regulating members 26, 27, and 28, etc., are formed of a synthetic resin and are nonmagnetic, under a nuclear magnetic resonance imaging (MRI) environment of picking up an image of information on the interior of a biological body by a nuclear magnetic resonance phenomenon with the tube 1 being inserted in the body, the tube does not negatively effect on image formation. Moreover, image formation under an MRI environment is also not deteriorated by the tube which utilizes vacuum pressure (negative pressure).

In addition, because the tube 1 is a bellows tube having protrusions 3 successive in a concavo-convex wavy shape, the adjoining protrusions 3 can form the latching-member receiving part 11 at any location in the lengthwise direction, so that the position of the latching member 7 can be set relatively freely.

In the first embodiment, all structural elements are formed of a nonmagnetic material. However, the holding members 8, 9, and 10 may be, for example, an Ni—Ti superelastic alloy wire with superior flexibility, or a memory alloy having a linear shape memorized beforehand, or, the direction regulating members 26, 27, and 28 each may be a stainless steel wire.

Other embodiments will be explained below. The same structural element will be denoted by the same reference numeral through the other embodiments, and the detailed explanation thereof will be skipped to avoid redundancy.

Second Embodiment

Figure 8:
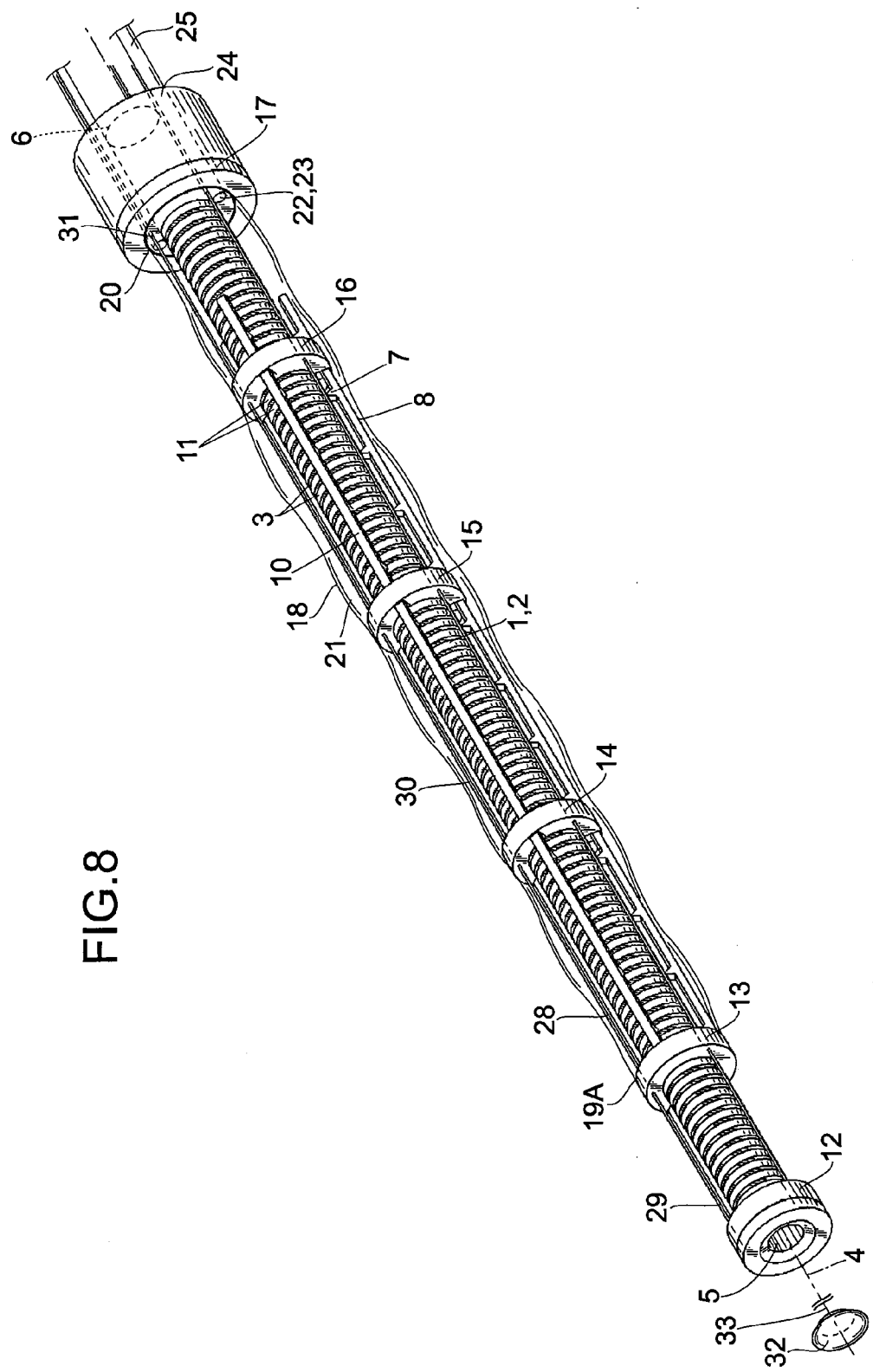
FIG. 8 is a perspective view showing a second embodiment of the present invention in a straight condition with a closing cover being partially cut out.

FIG. 8 shows a second embodiment. A leading end 19A is coupled to the second spacer 13, and the closing cover 18 is provided from the second spacer 13 to the sixth spacer 17. Moreover, the leading-end opening 5 is provided with an opening/closing body 32 which opens/closes the leading-end opening 5. The opening/closing body 32 is a discoid which fits into the leading-end opening 5 and plugs it, and, a flexible pulling member 33 which is, for example, in a linear shape, has one end coupled to the opening/closing body 32, and has another end provided at the basal-end opening 6 side.

Accordingly, like the first embodiment, the tube 1 in a flexible state is inserted in a body with the leading-end opening 5 being plugged by the opening/closing body 32 beforehand. At this time, because the opening is plugged by the opening/closing body 32, so that it is possible to prevent any organs from entering into the leading-end opening 5. Moreover, as the closed space 21 is set to be in a negative pressure condition, the latching members 7 are caused to engage with respective latching-member receiving parts 11, thereby making the tube 1 rigid. The leading end side of the tube 1 is still flexible even though the tube is in a rigid state, so that as the direction regulating members 26, 27, and 28 are manipulated at the basal-end opening 6 side, the direction of the leading-end opening 5 can be freely set at any time. As the basal end side of the pulling member 33 is pulled, the opening/closing body 32 is removed from the leading-end opening 5, and is retrieved through the basal-end opening 6 through the interior of the tube 1.

In this fashion, when the leading-end opening 5 is opened and the tube 1 is in a rigid state, the flexible surgical instrument A is inserted from the basal-end opening 6 side, and is caused to protrude from the leading-end opening 5 for use.

As explained above, according to the second embodiment, as the leading-end opening 5 is provided with the opening/closing body 32, when the tube 1 is inserted in a body, the leading-end opening 5 is closed to prevent any organs from entering thereinto.

Third Embodiment

Figure 9:
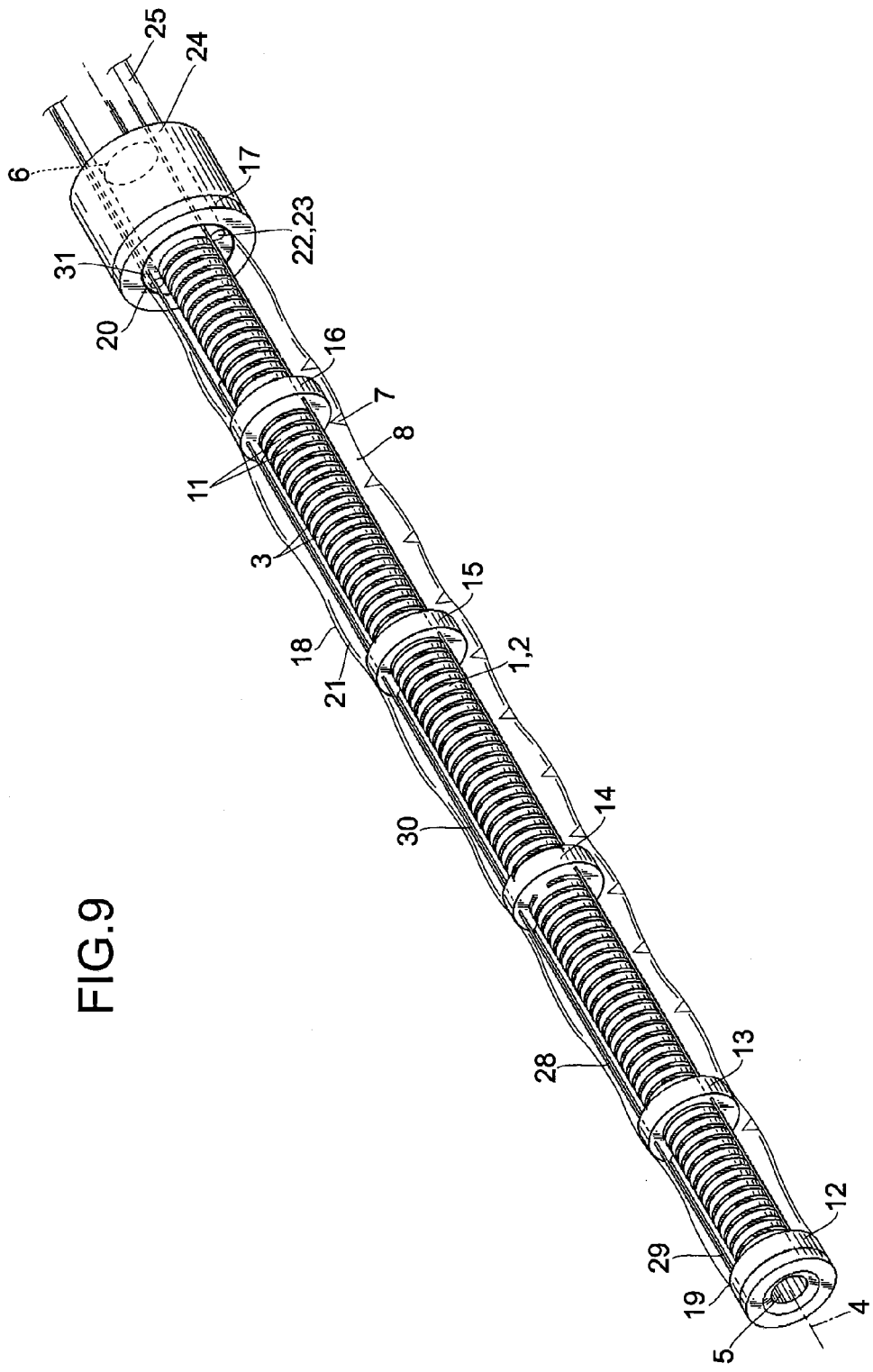
FIG. 9 is a perspective view showing a third embodiment of the present invention in a straight condition with a closing cover being partially cut out.
Figure 10:
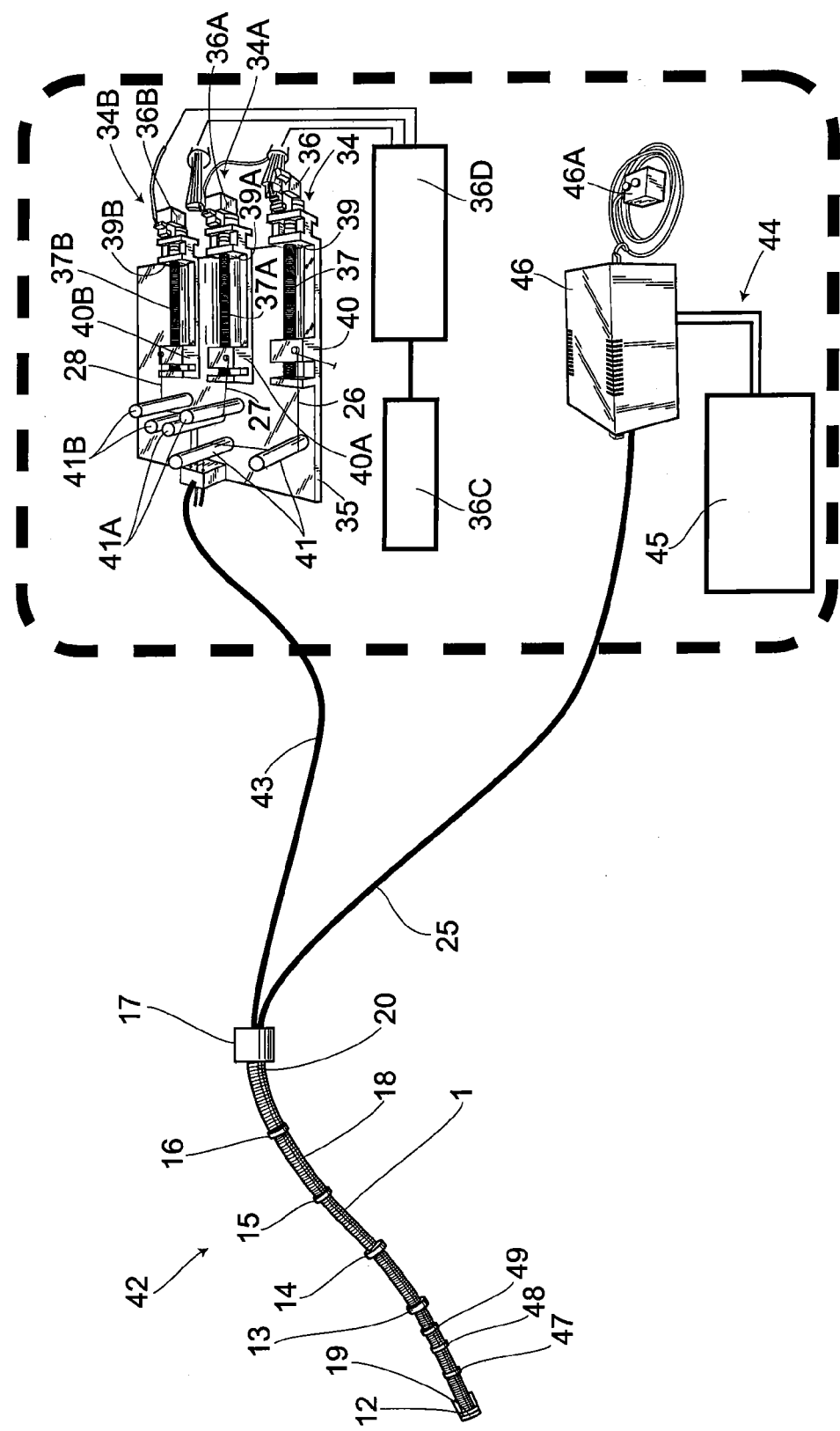
FIG. 10 is a schematic perspective view showing a fourth embodiment of the present invention.
Figure 11:
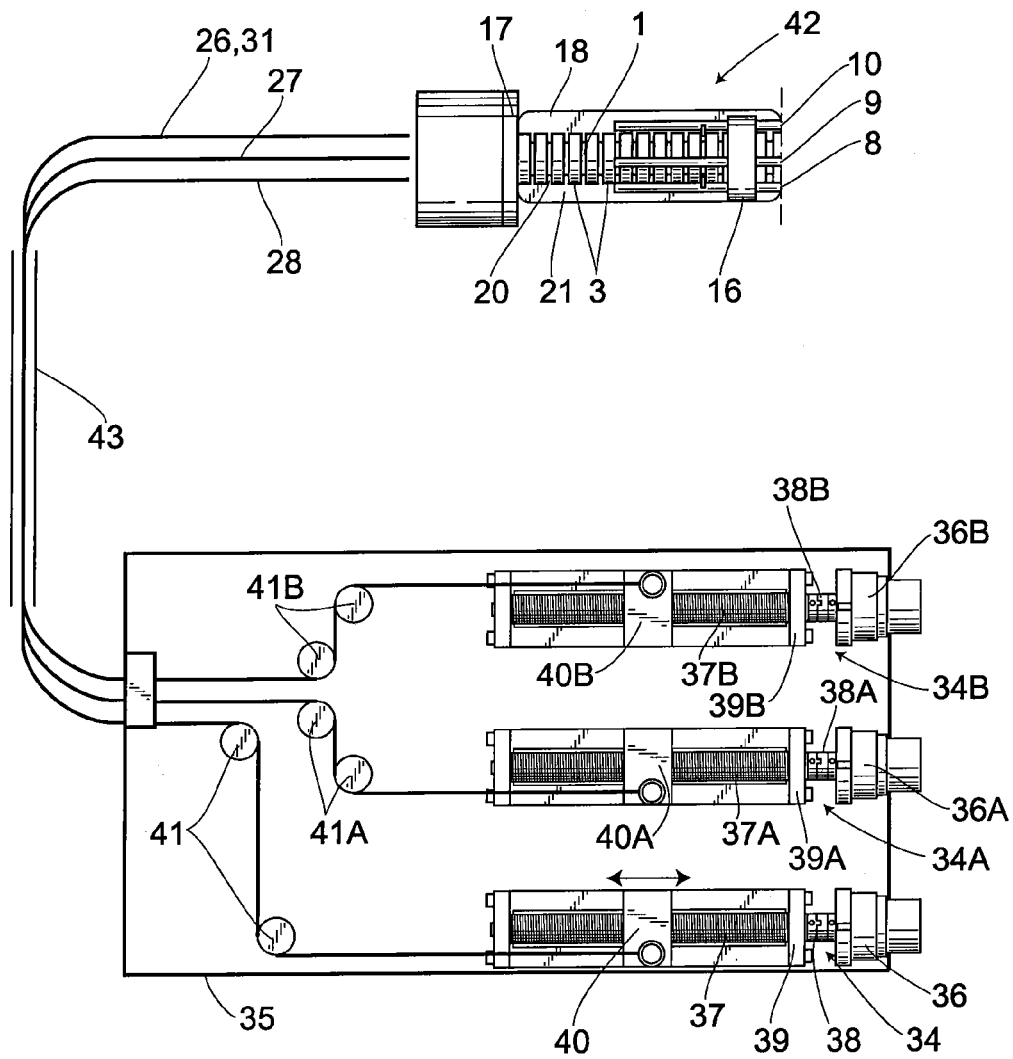
FIG. 11 is a plan view of the fourth embodiment.
Figure 12:
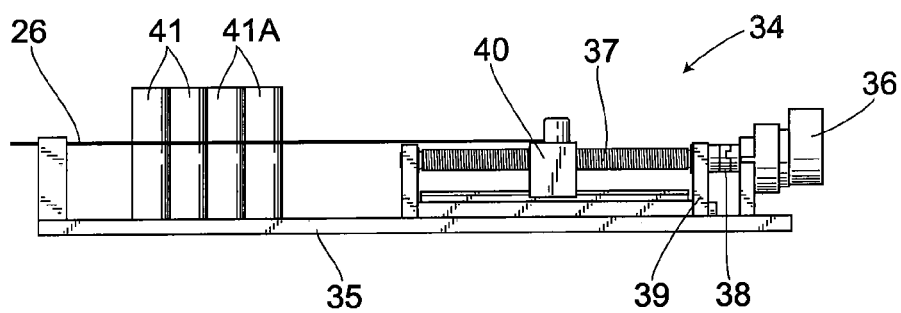
FIG. 12 is a side view of the fourth embodiment.

FIG. 9 shows a third embodiment. Unlike the first and second embodiments in which the latching members 7 are provided via the holding members 8, 9, and 10, the closing cover 18 itself is provided with the latching members 7.

Therefore, according to the third embodiment, when the closed space 21 is subjected to pressure reduction from an atmospheric pressure condition, the closing cover 18 reduces its diameter with the latching members 7 being positioned in the lengthwise direction by the closing cover 18 itself, and the latching members 7 move toward the axis 4 along with such diameter reduction operation, and engage with respective latching-member receiving parts 11, thereby making the tube 1 rigid.

As explained above, according to the third embodiment, as the latching members 7 are directly provided on the closing cover 18, the number of parts can be reduced as much as possible, thereby accomplishing further reduction in size of the apparatus, further improvement of a failure rate, etc.

Fourth Embodiment

FIGS. 10 to 14 show a fourth embodiment. In the fourth embodiment, a motor-driven driving device is provided which is for driving each of the first to third direction regulating members 26, 27, and 28 each formed of, for example, a wire like a fluorocarbon wire. Another end 31 of the first direction regulating member 26 is connected to a first driving device 34. Likewise, the second and third direction regulating members 27, 28 are connected to second and third driving devices 34A, 34B, respectively. The first driving device 34 has a first ultrasonic motor 36 fixed on the top face of a base plate 35. The rotating/driving shaft of the first ultrasonic motor 36 is coupled to a first male-screw bar 37 on an extended line via a first coupler 38 so-called a couple ring. The first male-screw bar 37 has both ends rotatably supported by a pair of first bearings 39 provided on the base plate 35. A first moving body 40 having a female screw (not illustrated) which can be threaded with the first male-screw bar 37 and being so-called a slider is provided in a reciprocal manner along the lengthwise direction of the first male-screw bar 37. The first moving body 40 is coupled to another end 31 of the first direction regulating member 26. Another end 31 of the first direction regulating member 26 is hooked on first wire guide protrusions 41 standingly provided on the base plate 35 to make the direction of another end 31 adjustable. Note a the flexibility/rigidity adjustable apparatus 42 comprising the tube 1, the holding members 8, 9, and 10, the spacers 12, 13, 14, 15, and 16, the closing cover 18, etc., and the first bearing 39 are formed of PTFE, the first moving body 40 and the first wire guide protrusion 41 are formed of polyacetal, the first male-screw bar 37 is formed of polyamide, and the first coupler 38 is formed of a stainless steel like SUS304, so that structural elements other than the first coupler 38 are nonmetals.

Accordingly, as the first ultrasonic motor 36 is actuated, the first male-screw bar 37 rotates in a clockwise direction or in a counterclockwise direction, so that a rotational motion of the first moving body 40 is converted into a linear motion by a feed screw mechanism, and as a result, the first direction regulating member 26 is fed out toward the flexibility/rigidity adjustable apparatus 42 or pulled back therefrom to make the flexibility/rigidity adjustable apparatus 42 extended or bent.

Likewise, the second and third driving devices 34A, 34B have second and third ultrasonic motors 36A, 36B, respectively, on the top face of the base plate 35, the rotating/driving shafts of the ultrasonic motors 36A, 36B are coupled to second and third male-screw bars 37A, 37B, respectively, via second and third couplers 38A, 38B, respectively. Both ends of each second and third coupler 38A, 38B are rotatably supported by a pair of second bearings 39A, and a pair of third bearings 39B provided on the base plate 35. Note that the ultrasonic motors 36, 36A, 36B are connected to a controller 36C with an operating unit for manual operation, and as the controller 36C is manipulated, the ultrasonic motors 36, 36A, and 36B are controlled through a motor control device 36D. Second and third moving bodies 40A, 40B which can be threaded with the second and third male-screw bars 37A, 37B, respectively, are provided in a reciprocal manner along the lengthwise directions of the second and third male-screw bars 37A, 37B, and the second and third moving bodies 40A, 40B are coupled to the second and third direction regulating members 27, 28, respectively. The second and third direction regulating members 27, 28 are hooked on second and third wire guide protrusions 41A, 41B, respectively, standingly provided on the base plate 35 to make respective directions of the second and third direction regulating members adjustable.

A flexible tube 43 which serves as a guide tube is present between the flexibility/rigidity adjustable apparatus 42 and the base plate 35, and the first to third direction regulating members 26, 27, and 28 pass all the way through the interior of the flexible tube 43.

The first to third driving devices 34, 34A, and 34B are arranged at a non-clean area together with a negative pressure adjusting device 46 connected to the intake/exhaust pipe 25 and including an operating unit 46A for an intake/exhaust changeover valve device or the like having a negative pressure source 45 like an air pump, separately from the flexibility/rigidity adjustable apparatus 42 present at a clean area.

In the fourth embodiment, the first to sixth spacers 12, 13, 14, 15, 16, and 17 are provided at equal clearances between the leading end 19 of the tube 1 and the basal end 20, and furthermore, seventh to ninth spacers 47, 48, and 49 are provide at equal clearances between the first and second spacers 12, 13 arranged at the leading end 19 side. Across the seventh to ninth spacers 47, 48, and 49, like the other second to fifth spacers 13, 14, 15, and 16, the first to third holding members 8, 9, and 10, the closing cover 18, the first to third direction regulating members 26, 27, and 28, etc., are provided. Accordingly, regarding the arrangement of the spacers at the leading end side of the tube 1, i.e., the first and second spacers 12, 13, and the seventh to ninth spacers 47, 48, and 49 have a shorter clearance between individual spacers in the fourth embodiment in comparison with other spacers, i.e., the third to sixth spacers 14, 15, 16, and 17.

Therefore, as the first to third driving devices 34, 34A, and 34B are actuated to feed or pull back the first to third direction regulating members 26, 27, and 28 to thereby bend the flexibility/rigidity adjustable apparatus 42 in a desired direction, and as an air intake/exhaust device 44 is actuated to evacuate air through the inlet/outlet parts 22 to thereby change the pressurized condition of the closed space 21 from an atmospheric pressure condition to a negative pressure condition, the closing cover 18 reduces its diameter around the axis 4, and the latching members 7 are caused to engage with respective latching-member receiving parts 11, thereby changing the state of the tube from a flexible state to a rigid state by evacuation of air. Hence, when the tube 1 is inserted in a body, the tube is made in a flexible state by introduction of air, and after the tube is inserted, the state of the tube can be freely changed to a rigid state by evacuating air.

Figure 13:
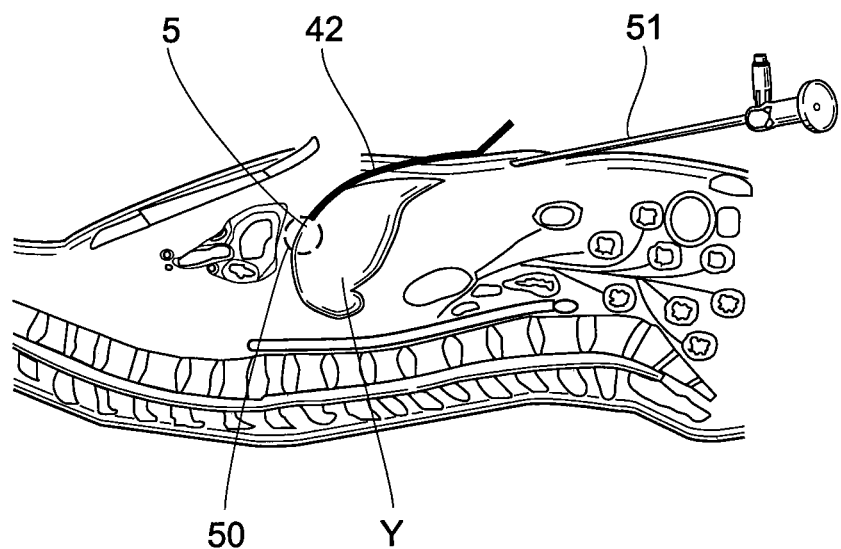
FIG. 13 is a schematic diagram showing a use situation.
Figure 14:
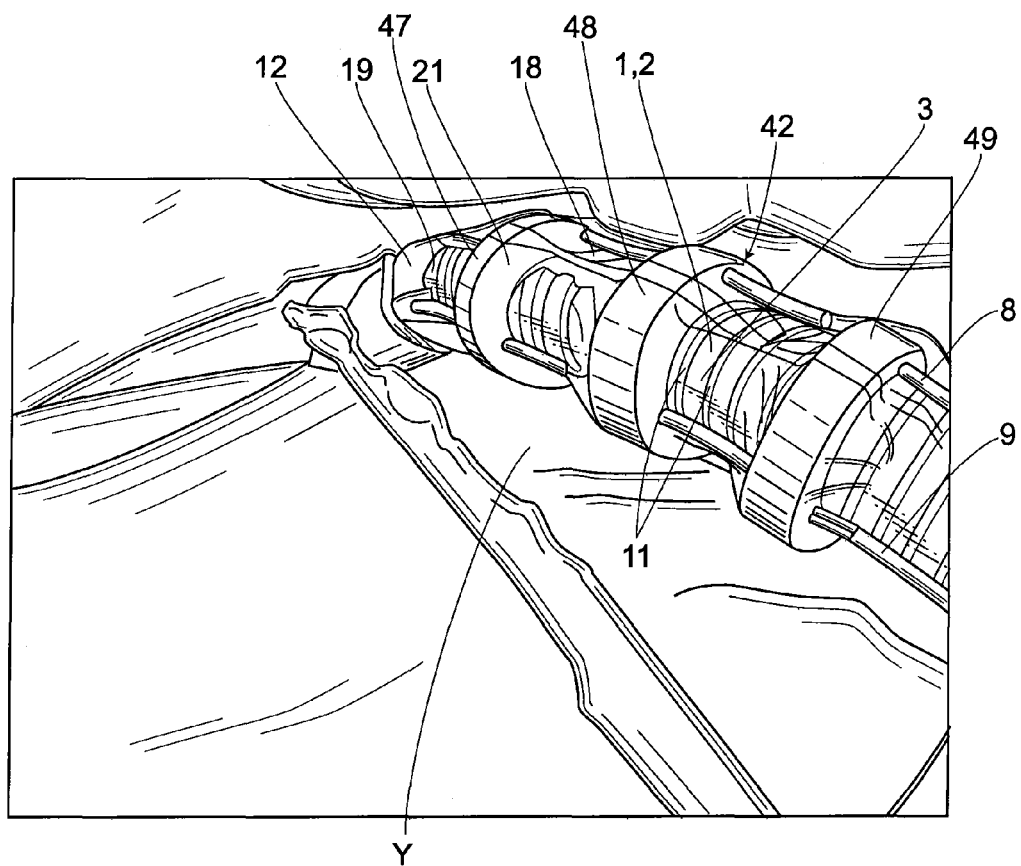
FIG. 14 is a perspective view showing a use situation.

As shown in FIGS. 13 and 14, it is possible for a user to insert the flexibility/rigidity adjustable apparatus 42 while checking how the flexibility/rigidity adjustable apparatus 42 enters in, for example, a bowel Y of a pig through a scope 51 in a vivio experiment.

As explained above, according to the fourth embodiment, the first to third direction regulating members 26, 27, and 28 are connected to the first to third driving devices 34, 34A, and 34B, respectively, driven by respective first to third ultrasonic motors 36, 36A, and 36B. As respective tensions of the first to third direction regulating members 26, 27, and 28, and thus feeding/pulling back thereof are automatically controlled, the bending direction of the flexibility/rigidity adjustable apparatus 42 can be automatically adjusted, and a remote control thereof is enabled, resulting in accomplishment of cleanliness.

Furthermore, the seventh to ninth spacers 47, 48, and 49 are provided between the first and second spacers 12, 13 in addition to the first to fifth spacers 12, 13, 14, 15, and 16. Arrangement of the larger number of spacers at the leading end side of the tube 1 than other portions thereof ensures improvement of the rigidity of the leading end side when in a rigid state.

Fifth Embodiment

Figure 15:
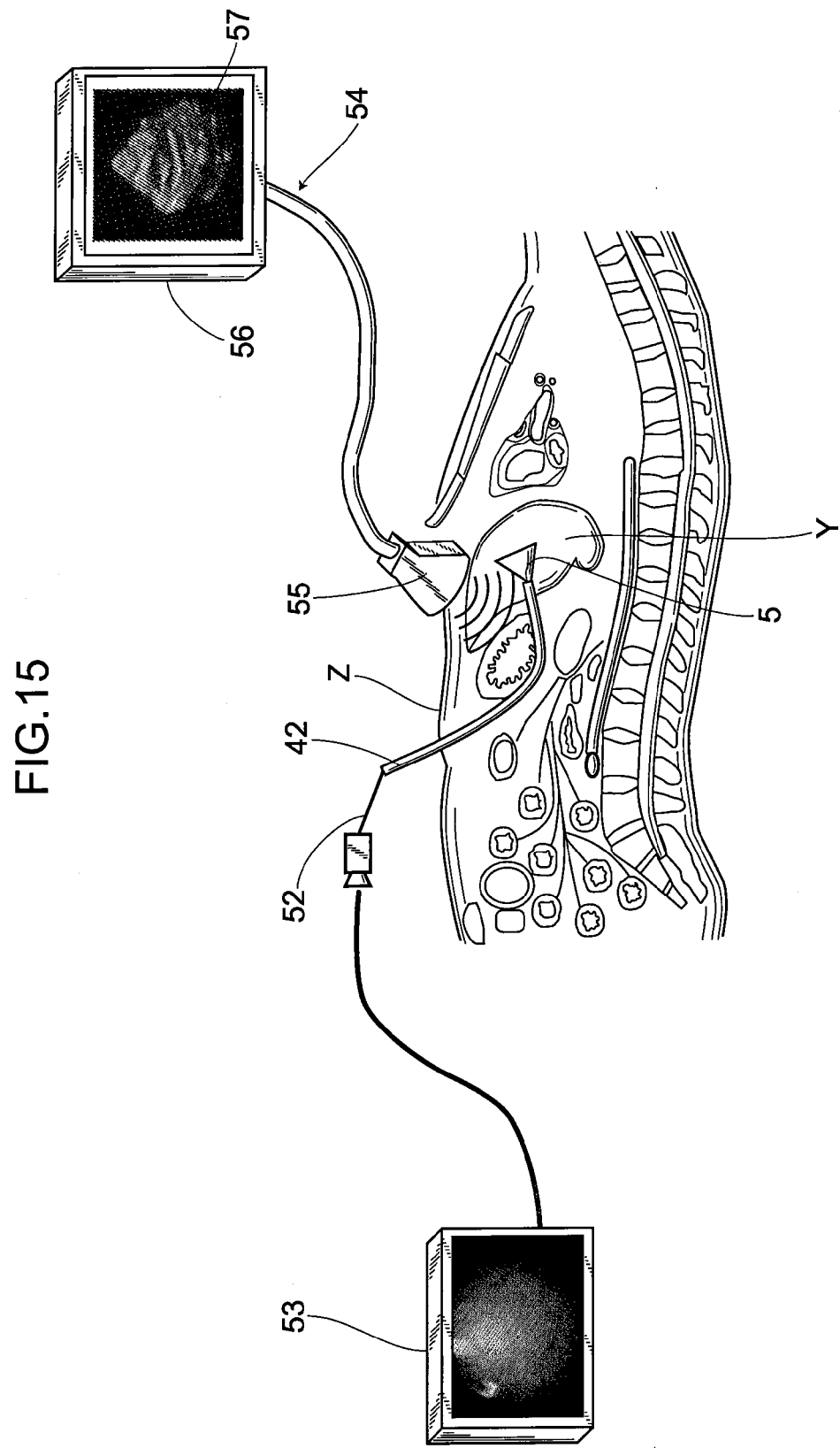
FIG. 15 is a schematic diagram showing a fifth embodiment of the present invention.

FIG. 15 shows a fifth embodiment. In the fifth embodiment, in a case in which a port is formed in an abdominal area through which the flexibility/rigidity adjustable apparatus 42 is inserted in, for example, a bowel Y of a pig in a vivio experiment without any securing of a space, such as aeroperitoneum or raising, at all to evaluate how the flexibility/rigidity adjustable apparatus 42 is inserted, a leading end of a fiber scope 52 is caused to pass all the way through the tube 1 of the flexibility/rigidity adjustable apparatus 42 to monitor the exterior through the leading-end opening 5. The fiber scope 52 is connected to a first display device 53 like a television monitor which displays an image. Conversely, an ultrasound diagnosis apparatus enables a diagnosis over a skin Z near the bowel Y. An ultrasound diagnosis apparatus 54 emits ultrasound to an object and visualizes the reflection thereof, to thereby carry out an image inspection technique which enables inspection of the internal condition of the object in a nondestructive manner. The ultrasound diagnosis apparatus comprises a probe 55 which has a mechanism of generating ultrasound and receiving reflected ultrasound, a processing device 56 which processes received data, and a second display device 57 which displays the processed image in real time.

The flexibility/rigidity adjustable apparatus 42 is inserted in a manner explained above, and the fiber scope 52 is caused to pass all the way through the flexibility/rigidity adjustable apparatus 42, so that it becomes possible to visually observe the condition of the bowel Y through the first display device 53. Conversely, the probe 55 is arranged over the skin Z near the bowel Y, ultrasound is generated, and data representing reflected ultrasound is displayed on the second display device 57 through the processing device 56.

As the ultrasound diagnosis device 54 is used, it becomes fine even if the flexibility/rigidity adjustable apparatus 42 becomes invisible from the exterior when inserted in a body. In order to check the insertion condition, an endoscope image or an MRI (nuclear magnetic resonance image) may be utilized, but the endoscopic image alone does not enable confirmation of a position and a posture. In contrast, utilization of an MRI leads to increasing of a device in size. However, as the insertion condition of the flexibility/rigidity adjustable apparatus 42 is checked by the ultrasound diagnosis apparatus, a real-time image can be acquired with a good image quality.

In the case of a two-dimensional image pickup, the flexibility/rigidity adjustable apparatus 42 is likely to be affected by artifact. This is because air is present in the abdominal area. Conversely, when a liquid like water is filled in the closed space 21 instead of air, it becomes possible to suppress any influence of artifact.

In the case of a three-dimensional image pickup, as the flexibility/rigidity adjustable apparatus 42 enables image pickup around the leading end thereof, so that the flexibility/rigidity adjustable apparatus can be manipulated based on a picked-up image.

The flexibility/rigidity adjustable apparatus of the present invention can be applied to various fields including general industrial machineries in addition to medical engineering. The present invention is not limited to the forgoing embodiments, and can be changed and modified within the scope and spirit of the present invention.

The invention claimed is:

1. A flexibility/rigidity adjustable apparatus comprising:
   a flexible, long and thin member;
   a closing cover which covers an exterior of an outer circumference of the long and thin member, and which is able to expand/shrink around an axis of the long and thin member;
   a fluid inlet/outlet part connected to a closed space formed between the closing cover and the outer circumference of the long and thin member;
   a latching-member receiving part provided at the outer circumference of the long and thin member;
   a latching member which is able to, together with a shrinkage operation of the closing cover, engage with the latching-member receiving part;
   spacers fixed to the long and thin member along a lengthwise direction of the axis of the long and thin member with a clearance; and
   a holding member of the latching member having flexibility and restoring elastic force to return the holding member to a linear shape provided between the spacers for preventing the latching member from contacting the latching-member receiving part when the long and thin member is in a flexible state.

2. The flexibility/rigidity adjustable apparatus according to claim 1, wherein the long and thin member is a tube having a leading end and a basal end opposite to the leading end both opened.

3. The flexibility/rigidity adjustable apparatus according to claim 2, wherein the basal end of the tube is provided with the fluid inlet/outlet part.

4. The flexibility/rigidity adjustable apparatus according to claim 2, wherein the latching member is formed together with the closing cover.

5. The flexibility/rigidity adjustable apparatus according to claim 2, further comprising a direction regulating member which has one end coupled to a leading end of the tube, is provided along a lengthwise direction of the axis of the tube, and has another end provided at the basal end side of the tube.

6. The flexibility/rigidity adjustable apparatus according to claim 2, wherein the latching member and the latching-member receiving part facing the latching member are provided in at least two radial directions around the axis of the tube.

7. The flexibility/rigidity adjustable apparatus according to claim 2, further comprising an opening/closing body which opens/closes the opening of the leading end of the tube.

8. The flexibility/rigidity adjustable apparatus according to claim 1, wherein all of the structural elements are formed of a non-magnetic material.

9. The flexibility/rigidity adjustable apparatus according to claim 5, wherein a basal end of the direction regulating member is coupled to a motor-driven driving device.

10. The flexibility/rigidity adjustable apparatus according to claim 1, wherein a clearance between adjoining spacers is set to be narrower at the leading end side of the long and thin member than at other portions of the long and thin member.

11. The flexibility/rigidity adjustable apparatus according to claim 1, wherein a fiber scope is inserted in the long and thin member.

* * * * *